(12) United States Patent
Vitello et al.

(10) Patent No.: US 10,912,898 B1
(45) Date of Patent: Feb. 9, 2021

(54) TAMPER EVIDENT CAP FOR MEDICAL FITTING

(71) Applicant: Medical Device Engineering LLC, Pompano Beach, FL (US)

(72) Inventors: Jonathan J. Vitello, Fort Lauderdale, FL (US); Patrick Vitello, Fort Lauderdale, FL (US); Timothy Brandon Hunt, Hollywood, FL (US)

(73) Assignee: MEDICAL DEVICE ENGINEERING LLC, Pompano Beach, FL (US)

( * ) Notice: Subject to any disclaimer, the term of this patent is extended or adjusted under 35 U.S.C. 154(b) by 209 days.

(21) Appl. No.: 15/908,237

(22) Filed: Feb. 28, 2018

Related U.S. Application Data

(62) Division of application No. 14/613,080, filed on Feb. 3, 2015, now abandoned.
(Continued)

(51) Int. Cl.
*A61M 5/00* (2006.01)
*A61M 5/31* (2006.01)
(Continued)

(52) U.S. Cl.
CPC .......... *A61M 5/5086* (2013.01); *A61M 39/20* (2013.01); *A61M 39/1011* (2013.01); *A61M 2005/312* (2013.01)

(58) Field of Classification Search
CPC .............. A61M 5/5086; A61M 5/3202; A61M 2005/3104; A61M 39/20; A61M 2039/1033; A61J 1/18; B65D 41/3428
See application file for complete search history.

(56) References Cited

U.S. PATENT DOCUMENTS

| 732,662 A | 6/1903 | Smith |
|---|---|---|
| 1,678,991 A | 7/1928 | Marschalek |

(Continued)

FOREIGN PATENT DOCUMENTS

| EP | 0148116 A | 7/1985 |
|---|---|---|
| WO | WO 2008000279 | 1/2008 |
| WO | WO 2017086607 | 5/2015 |

*Primary Examiner* — Manuel A Mendez
*Assistant Examiner* — Justin L Zamory
(74) *Attorney, Agent, or Firm* — Malloy & Malloy, PL; Jennie S. Malloy

(57) ABSTRACT

A tamper evident closure assembly for a fitting including, but not limited to, use in combination with a female fixture or an enteral fixture. A cap is connectable in flow restricting relation to the fitting and includes an indicator member removably connected to an exterior thereof. A housing is dimensioned to removably contain the cap and the connected indicator member. Subsequent to the fixture being connected to the cap, a removal thereof results in the indicator member being detached from the cap and movably disposed in a captured, detached orientation within the housing. Tampering may be evidenced by the indicator member remaining captivated within the housing which may be determined by visual observation or the generation of sound caused resulting from the housing being shaken. An included drive assembly is structured for concurrent rotation of the housing and the indicator member one direction and relative movement there between upon rotation of at least a housing in an opposite direction.

9 Claims, 7 Drawing Sheets

Related U.S. Application Data

(60) Provisional application No. 61/937,874, filed on Feb. 10, 2014, provisional application No. 61/936,044, filed on Feb. 5, 2014, provisional application No. 61/935,096, filed on Feb. 3, 2014.

(51) Int. Cl.
*A61M 5/50* (2006.01)
*A61M 39/20* (2006.01)
*A61M 39/10* (2006.01)

(56) References Cited

U.S. PATENT DOCUMENTS

| | | |
|---|---|---|
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 7/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,049,129 A | 9/1991 | Zdeb et al. |
| 5,057,093 A | 10/1991 | Clegg et al. |
| D323,392 S | 1/1992 | Byrne |
| 5,135,496 A | 8/1992 | Vetter et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,380,295 A | 1/1995 | Vacca |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,829,589 A | 11/1998 | Nguyen et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |

(56) References Cited

U.S. PATENT DOCUMENTS

| | | |
|---|---|---|
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,055,273 B2 | 6/2006 | Roshkoff |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,443,999 B1 | 5/2013 | Reinders |
| D684,057 S | 6/2013 | Kwon |
| 8,512,277 B2 | 8/2013 | Del Vecchio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 * | 8/2016 | Vitello ................ A61M 5/5086 |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,376,655 B2 | 8/2019 | Pupke et al. |
| D859,125 S | 9/2019 | Weagle et al. |
| 10,758,684 B1 | 9/2020 | Vitello et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 * | 4/2006 | Dionigi ................ A61M 5/283 |
| | | 604/181 |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |

(56) References Cited

U.S. PATENT DOCUMENTS

| | | |
|---|---|---|
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1 | 7/2015 | Okihara |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0319438 A1 | 11/2017 | Davis et al. |
| 2017/0354792 A1 | 12/2017 | Ward |
| 2018/0001540 A1 | 1/2018 | Byun |
| 2018/0078684 A1 | 3/2018 | Peng et al. |
| 2018/0089593 A1 | 3/2018 | Patel et al. |

\* cited by examiner

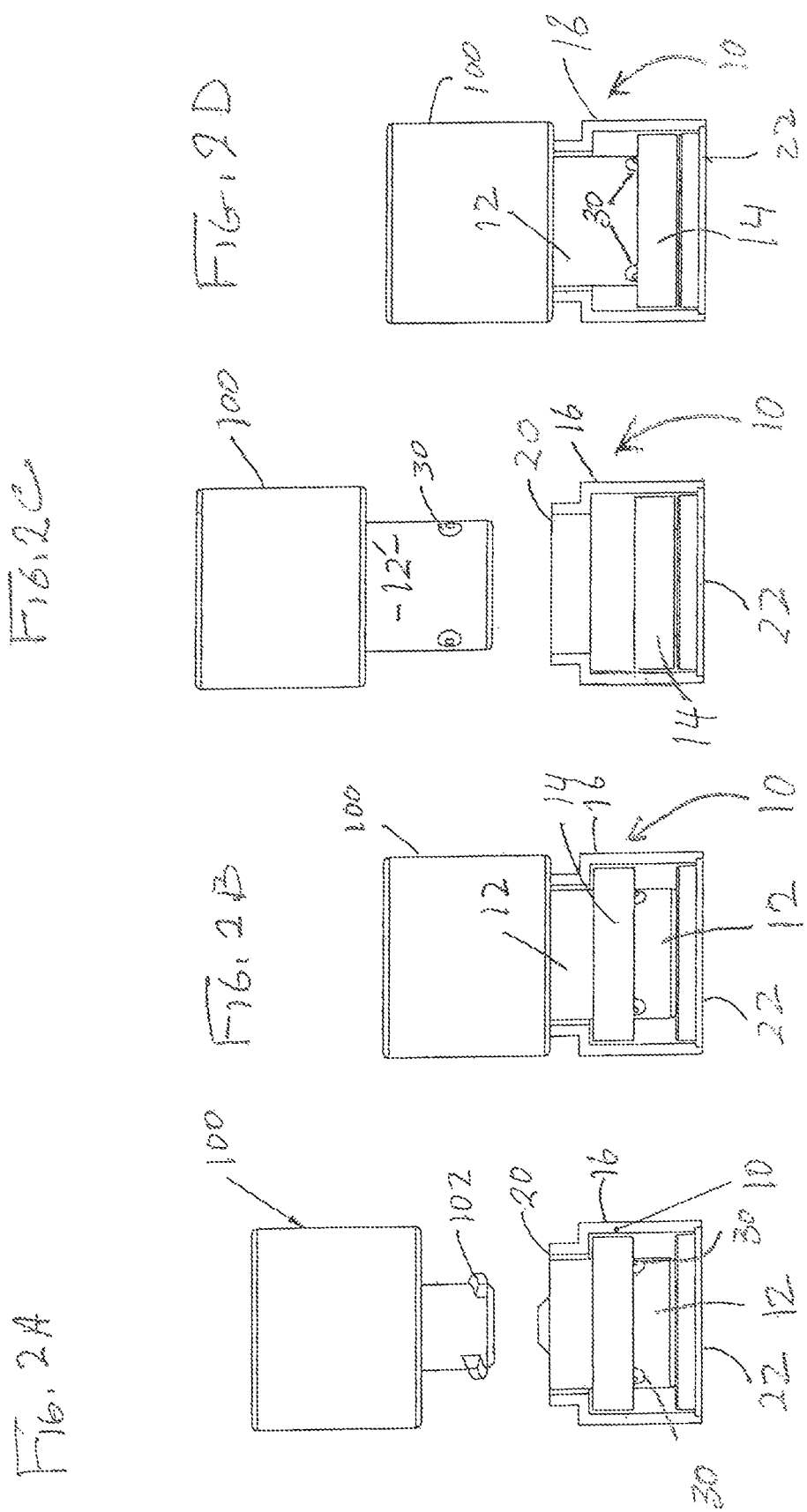

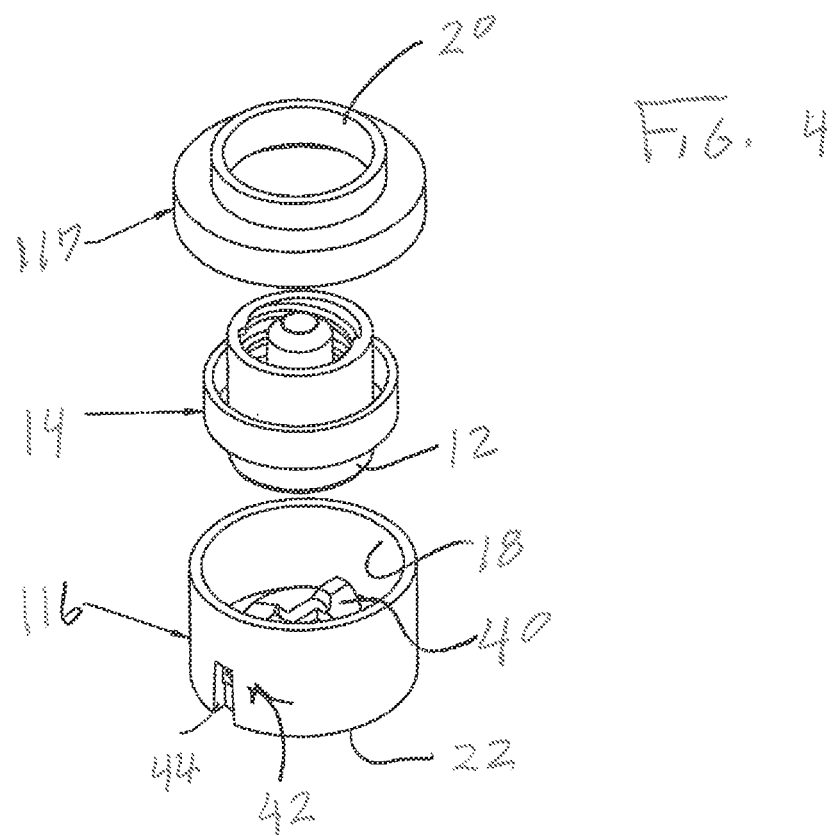
FIG. 4
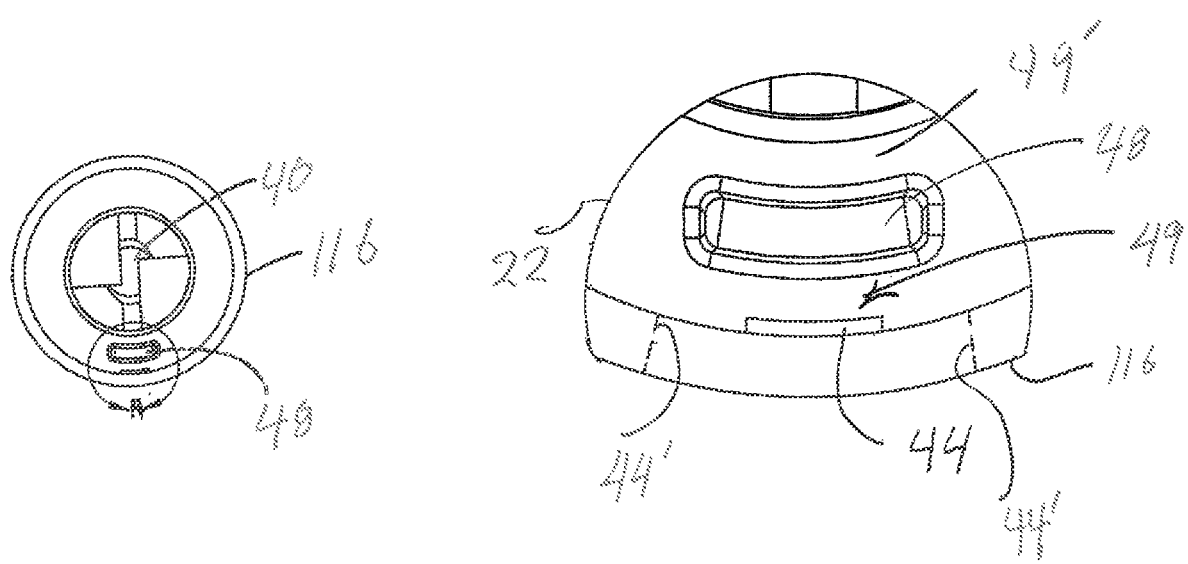
FIG. 7
FIG. 7A

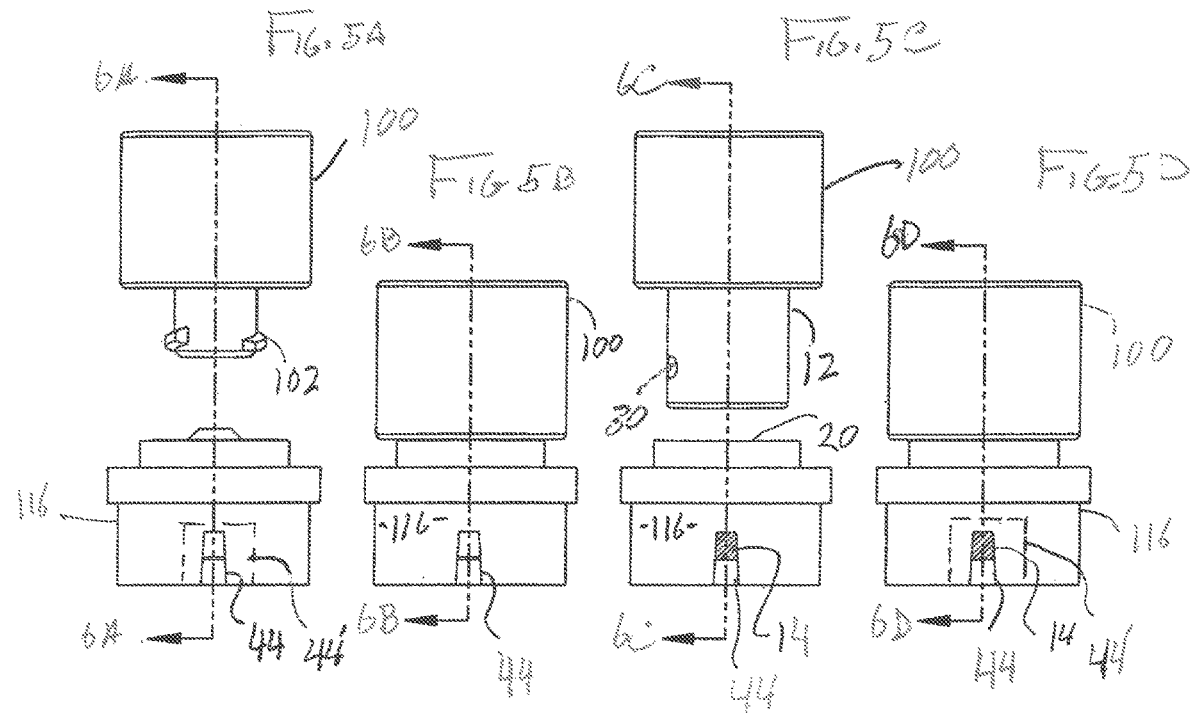
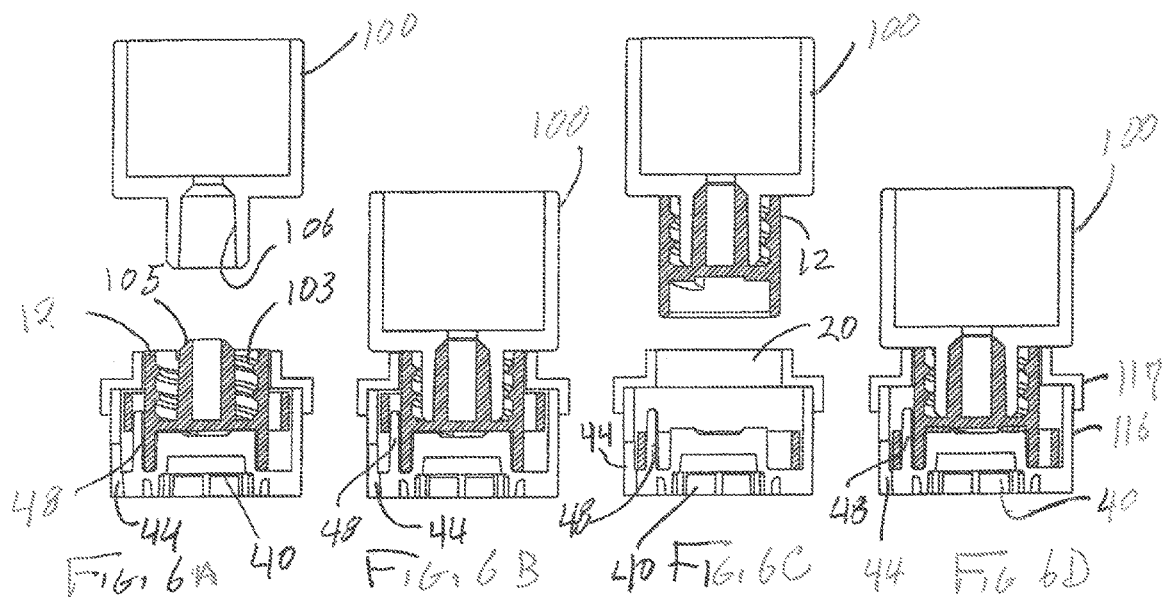

TAMPER EVIDENT CAP FOR MEDICAL FITTING

CLAIM OF PRIORITY

The present application is a divisional application of a previously filed, currently pending application having Ser. No. 14/613,080, filed on Feb. 3, 2015, which claims priority to a previously filed, U.S. Provisional patent application having Ser. No. 61/937,874 and a filing date of Feb. 10, 2014, as well as to another previously filed U.S. Provisional application, namely, that having Ser. No. 61/936,044 filed on Feb. 5, 2014, and to one additional previously filed, U.S. Provisional application, namely that having Ser. No. 61/935,096 filed on Feb. 3, 2014, the contents of all of which are incorporated herein by reference in their entireties.

BACKGROUND OF THE INVENTION

Field of the Invention

This invention is directed to a tamper evident closure assembly for use with a fitting for a medical device including, but not limited to, a female fitting and/or an enteral female fitting. The closure assembly includes a flow restrictive cap having an indicator member removably connected thereto and initially and removably disposed within a housing. Removal of the cap from the housing, once connected to the fitting, results in the detached indicator member being captured within the housing. Retention of the indicator member within the housing is determinative of use of the cap and possible evidence of tampering, upon an attempted reinsertion of the cap within the housing.

DESCRIPTION OF THE RELATED ART

In the medical field, it is a relatively common procedure for authorized medical personnel to order that a patient be given a drug or medication by injection or other procedures, including administering fluids to a patient by intravenous (IV) infusion. It is also relatively common procedure for a number of administering devices to be pre-loaded or filled by a pharmacist or other authorized personnel whether within the hospital or at another facility and location, which may be generally referred to as a filling station. However, a filling station is typically located in a remote part of the facility, relative to the patient care area where the injection is to be administered. Indeed, at large medical facilities, a filling station may resemble a facility on the hospital grounds from which drugs and other fluids are delivered to multiple nursing stations at different locations. Because of the remote location of many nurse's stations, relative to a filling station, a fluid or drug loaded administering device is very often given to another person for delivery to a nurse's station for subsequent dosing of the patient by a duly qualified nurse or other medically trained person. Also, and especially in the case where a drug has been prescribed and loaded in the administering device that is a very expensive or addictive, such as but not limited to morphine, there is a danger that the pre-loaded syringe or other administering device will be tampered with at some point, by a person seeking unauthorized access thereto. This possibility can present real danger in that if such person were to gain access to the prescribed medicine and then, inappropriately and without concern, substitute some other, unauthorized material in the syringe which looks like the actual prescribed medicine and dosage. By way of an example only, if saline solution were substituted for a dose of morphine or numerous other drugs, the result can be extremely serious. Thus, there is a problem of knowing if a sealed, preloaded syringe or other administering device has, or has not, been exposed to contamination or might otherwise have been compromised by its being tampered with. This and related types of problems have been described in one or more previously granted U.S. patents granted to one of the inventors herein, such as U.S. Pat. No. 5,328,474.

In addition to the administration of drugs, medicine, etc., meaningful protection is required in the use of enteral feeding sets, like medical devices and accessories. As commonly recognized in the medical and related professions, the term "enteral" relates to the administration or removal of fluid in the form of liquid or gas to or from the gastrointestinal tract. Moreover, enteral connectors and/or fixtures of the type referred to herein relate to medical devices or accessories which are intended for use in enteral applications. Further, small-bore connectors for enteral application may be employed for delivery of enteral nutrition fluid from a fluid source to the patient. Additionally, it is pointed out that enteral feeding sets and extension sets may include a female fixture, wherein the source of fluid flows to the patient initially through the female fixture and to and through a cooperatively structured male enteral fixture.

Also, with regard to administering fluids to a patient by intravenous (IV) infusion, a variety of IV assemblies are known and are useful in the treatment of a number of medical conditions, as a variety of fluids and/or medicines can be administered to a patient utilizing such assemblies over a prescribed period of time and in controlled amounts. In use, a conventional IV administration assembly typically includes a reservoir or container, in the form of a bottle or more commonly, a flexible material bag, suspended on a pole or like support structure located substantially adjacent to the patient being treated, typically in an elevated relation thereto. In addition, the IV fluid flows from the supported and elevated IV bag to the patient by means of elongated, flexible tubing connected at a proximal end to the IV bag and at the other distal end, connected intravenously to the patient by way of a catheter or like structure. The IV delivery tube is also structured to connect at one end to or be interconnected with an appropriate connector, often having somewhat of a "Y" shape, that is associated with the IV assembly and in fluid communication with either the contents of the IV bag or alternatively, with the catheter in use on the patient for intravenous administration of fluids and medicines.

One such connector may be in the form of a female connector attached to the IV bag or other container and disposed in fluid communication with the contents thereof. An appropriate female connector may be in the form of a female luer connector which at least partially defines, along with a male luer connector, a "luer lock" connector assembly, as is well known in the medical profession. The male luer connector is secured to the IV delivery tubing, such as at the proximal end, and is specifically structured to be attached to the female luer connector in a manner which establishes fluid communication with contents of the IV container, and facilitates a flow of the IV fluid from the IV container through the connected male and female luer connectors. As a result, fluid flow between the patient and the interior of the IV bag is established. As is also well known, various types of valves and/or flow regulating devices may be operatively associated with the IV assembly to regulate the amount of fluid or rate of fluid delivery to the patient during the administration procedure.

In addition, known IV containers or reservoirs may incorporate an additional female luer connector or other female type connector which are disposed in fluid communication with the IV delivery tubing, such as but not limited to at the IV bag. This additional female luer connector is provided to administer additional liquid agents, such as pain medication, antibiotics, and/or other medicinal compositions, to the IV fluid being delivered to the patient. However, such an additional female luer connector may remain unused or may be accessed at a time subsequent to the initiation of the IV fluid administration, such as when additional medication or another composition is required or prescribed.

In periods of non-use, it is important to maintain a female luer connector in a closed and fluid sealed condition in order to maintain sterility, and also, the integrity of the IV fluid prior to use. This is also important in order to restrict unauthorized access to the IV fluid and even to the female luer connector.

Therefore, and regardless of the known or conventional attempts to date to provide a fluid restricting closure to protect the contents of preloaded administering devices and/or enteral devices, certain problems still remain in this field of art. Accordingly, there is a need in this area for an improved, closure assembly which provides a secure and reliable fluid restricting or sealing connection to the discharge fixture or connector such as, but not limited to a female fixture associated with an enteral administering device. If any such new closure assembly were developed, it should also have additional structural and operative features which can provide a clear and reliable indication that use and/or attempted tampering with the patent administering device has occurred.

Further, if any such new closure assembly were developed it should include structural features capable of providing both visual and audible indications that tampering and/or use of the administering device has occurred. Also, any such closure assembly should be capable of use with little or no structural modification with a variety of different connectors, fixtures, administering devices, etc. Finally, any such improved closure assembly should also be structurally and operatively reliable, while still remaining cost effective to manufacture and assemble, in order to facilitate widespread use and acceptance throughout the medical profession.

SUMMARY OF THE INVENTION

The present invention is directed to a tamper evident closure assembly of the type which is attachable in flow restricting relation to a fitting. As explained in greater detail hereinafter, structural and operative features of the inventive closure assembly in one or more preferred embodiments, including components thereof, facilitate its connection in flow restricting relation to a female enteral fitting. Also, the closure assembly of the present invention is structured to provide a clear indication of use or attempted tampering with the closure assembly, such fitting and/or fluid source associated with the fitting.

As used herein and as commonly recognized, the term "enteral" relates to the administration or removal of fluid, in the form of liquid or gas, to or from the gastrointestinal tract. Moreover, enteral connectors and/or fixtures of the type referred to herein relate to medical devices or accessories which are intended for use in enteral applications. Further, small-bore connectors for enteral application may be employed for delivery of enteral nutrition fluid from a fluid source to the patient. Therefore, enteral feeding sets and extension sets may include a female fixture/connector, wherein fluid from the source the source flows to the patient initially through the female fixture and to and through a cooperatively structured and attached male enteral fixture. Accordingly, in order to restrict access and maintain the integrity of the source of fluid associated with the female fixture, the closure assembly of the present invention is structured to connect to the female enteral fixture in flow restricting relation thereto, prior to the interconnection of the female enteral fixture to the male enteral fixture.

As such, the various embodiments of the closure assembly of the present invention include operative and structural features which effectively accomplish a flow restricting connection to such a female fitting. At the same time, the closure assembly provides clear evidence of use of the fitting and/or associated fluid source as well tampering therewith in situations involving unauthorized use or access to the fitting and/or fluid source. However, it is emphasized that the various structural features of the one or more preferred embodiments of the closure assembly of the present invention are such that the invention is not limited to use with female fittings and/or female enteral fittings. To the contrary, the closure assembly of the present invention may be utilized to establish a flow restricting connection and closure of different fittings, connectors, etc. associated with a variety of different medical devices, accessories, etc. Such additional connectors/fittings with which the closure assembly of the present invention may be used include, but are not limited to, male Parental fittings, IV fittings; Luer fittings; Neuraxial fittings; Epidural fittings; anesthesia fittings, and potentially others, whether now known or yet to be developed and/or put into use.

Therefore, the closure assembly of the present invention comprises a cap connectable in flow restricting relation to a cooperatively structured fitting such as, but not limited to, the type specifically or generally referred to herein. Further, an indicator member preferably, but not necessarily, in the form of a ring or other type of annular structure is removably connected to an exterior of the cap and is movable therewith while still connected thereto. A housing having a hollow interior and an access opening is dimensioned and configured to contain the cap and connected indicator member within the housing. Moreover, the access opening is disposed, dimensioned and configured to allow passage of the cap there through at substantially the same time it is detached from the indicator member. Therefore, in at least one embodiment of the housing of the closure assembly, the access opening is disposed and dimensioned to restrict passage of the indicator member there through concurrently with the through passage of the cap. In use, an attempted removal of the cap from the housing, such as when the cap is connected to a corresponding fixture, results in a portion of the interior of the housing engaging and/or interfering with the indicator member causing its detachment from the cap.

In order to facilitate the removable connection of the indicator member and/or ring from the exterior of the cap at least one, but in certain practical applications, a plurality of frangible tabs are provided. The one or more tabs are formed from a frangible or breakable material and are interconnected between an exterior surface of the cap and an interior surface of the indicator member. In addition, the one or more frangible tabs are structured for generally precise breakage along a corresponding length thereof. As described in greater detail below, the breakage occurs along the length of the tab in spaced relation to both the exterior surface of the cap and an interior surface of the indicator member. As a result, a tab segment remains on both the exterior surface of the cap and an interior surface of the indicator member. One or both of the tab segments include an exposed face having a curvilinear or other predetermined configuration which restricts interfering engagement or a "hang-up" there-between subsequent to the disconnection of the indicator member from the exterior surface of the cap. Such an interfering engagement or hang-up could possibly result in a failure of the indicator member to assume a normally detached orientation from the cap, the latter being an intended goal of the invention in some embodiments. Accordingly, the breakage is disposed along the length of the one or more tabs at a location which ensures a clearance space existing between each tab segment and the oppositely disposed exterior or interior surfaces of the cap and indicator member, respectively.

As indicated, upon removal of the cap, such as when connected to a corresponding fixture, the indicator member will be captured within the interior of the housing. Accordingly, when captured, the indicator member will provide a clear indication that the cap has been used and/or at least removed from the interior of the housing. Further, upon an attempted reinsertion of the cap within the housing, the existence of the indicator member in a detached orientation from the cap, would be indicative of an attempted tampering with and/or unauthorized use of the closure assembly, fixture or fluid source with which the attached fixture is associated.

Further, the various preferred embodiments of the closure assembly provide one or more effective ways to determine the existence of the detached indicator member being captured within the housing in a detached orientation. Moreover, the detection of the captured indicator member may be accomplished by visual observation and/or by sound. More specifically, the structure and/or material from which the indicator member is formed is sufficient to facilitate a sound being generated upon manipulation, such as by shaking, of the housing, once the indicator member is detached from the cap. Such shaking of the housing will result in a "rattling" sound of the cap within the interior of the housing.

In addition, one or more embodiments of the housing may include a viewing structure formed therein. The viewing structure may take a variety of different forms such as, but not limited to, a portion and/or substantially the entirety of the sidewall of the housing being substantially transparent. As used herein, being "substantially transparent" is meant to include the material of the housing being at least translucent so as to allow at least minimal viewing within the housing. As a result, a user can determine the location and/or other physical characteristics of the indicator member being in either a detached orientation or an attached orientation.

Further by way of example, the viewing structure of the housing may be in the form of at least one viewing port or window that is preferably formed in a sidewall portion of the housing. The viewing port or window is disposed, dimensioned and structured to facilitate a visual observance of the interior of the housing, as well as one or more components of the closure assembly specifically including, but not limited to, the indicator member. A visual determination of the indicator member being in the attached orientation to the cap or a detached orientation therefrom, is also facilitated by an "identifier" incorporated on or in at least the indicator member. Such identifier is structured to facilitate a visual distinction between the indicator member and other components on the interior of the housing, possibly including interior portions of the housing itself. Further by way of example, the identifier may be in the form of a color coding, difference in surface textures, indicia, markings, pictorial displays, etc., all of which may be incorporated, individually or in combination, in the structure of the indicator.

Further by way of example, when a color coding is utilized as the identifier, the color of the indicator member is ideally selected so as to be clearly distinctive from the observable color of the cap, as well as the interior portions of the housing itself. As a result, the color coding will allow an observer to distinguish the component being viewed through the aforementioned viewing structure by distinguishing the various colors of the indicator member, cap, housing, etc. As a result, an observer will be able to easily determine whether or not the cap has been used and removed from the housing and/or whether tampering is being attempted or has occurred by virtue of the color of the component being visually observed through the viewing structure.

In addition, the closure assembly includes a drive assembly, which may be in the form of a "ramp and cliff" drive structure. More specifically, a first ramp and cliff drive segment is formed on the cap and a second ramp and cliff drive segment is formed on the housing, in movable and/or mating engagement with the first ramp and cliff drive segment. The first and second drive segments are cooperatively structured to define a concurrent single direction, driven rotation of said cap and said housing. In at least one preferred embodiment, the drive assembly is disposed in an exterior location, as versus a central location, on both the sidewall or skirt portion of the cap and the interior bottom or interior end surface of the housing. As such, the first drive segment is formed on and extending along an outer circumferential edge of a skirt or like sidewall portion of the cap. In cooperation there with, the second drive segment is formed on an inner surface of the housing in corresponding relation to the first segment, so as to accomplish the movable interactive engagement therewith.

Therefore, the one or more preferred embodiments of the closure assembly of the present invention provide an efficient and reliable structure for closing, sealing and providing a clear indication of prior use of a cooperatively structured fitting such as, but not limited to an enteral female fitting or other female connector or fitting of the type which may be associated with a fluid source and attendant medical device. The closure assembly is further structured to provide a clear indication of tampering or attempted access to the fixture and/or fluid source with which the fixture may be associated.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 2A is a front view of the embodiment of FIG. 1 in an uninstalled state.

FIG. 2B is a front, partial interior view of the embodiment of FIG. 1 in an installed state.

FIG. 2C is a front partial interior view of the embodiment of FIG. 1 wherein a cap of the closure assembly is connected to a fixture and removed from the housing in a used state.

FIG. 2D is a front partial interior view of the embodiment of FIG. 1 wherein the cap and attached fixture is used and reinserted in the housing.

FIG. 3A is a detail view in partial cutaway of the structural features of FIG. 3.

FIG. 4 is a perspective view in exploded form of yet another preferred embodiment of the closure assembly of the present invention.

FIG. 5A is a front view of the embodiment of FIG. 4 in an uninstalled state.

FIG. 5B is a front, partial interior view of the embodiment of FIG. 4 in an installed state.

FIG. 5C is a front partial interior view of the embodiment of FIG. 4 wherein a cap of the closure assembly is connected to a fixture and removed from the housing in a used state.

FIG. 5D is a front partial interior view of the embodiment of FIG. 4 wherein the cap and attached fixture is used and reinserted in the housing.

FIG. 6A is a sectional view along line 6A-6A of FIG. 5A.
FIG. 6B is a sectional view along line 6B-6B of FIG. 5B.
FIG. 6C is a sectional view along line 6C-6C of FIG. 5B.
FIG. 6D is a sectional view along line 6D-6D of FIG. 5D.

FIG. 7 is a sectional view of one structural modification associated with the one or more preferred embodiments of the closure assembly of the present invention, including FIG. 4.

FIG. 7A is a detailed view in partial cutaway of segment "A" of FIG. 7.

Like reference numerals refer to like parts throughout the several views of the drawings.

DETAILED DESCRIPTION OF THE INVENTION IN THE PREFERRED EMBODIMENTS

As represented throughout the accompanying Figures and with initial reference to FIGS. 1 and 2A-2D, the present invention is directed to a closure assembly generally indicated as 10. Further, the closure assembly 10 is structured for use with a corresponding and/or cooperatively structured connector or fitting generally indicated as 100 and shown in FIGS. 2A-2D. Further, the fitting 100 may include a female fitting. In addition, the closure assembly 10 is structured to provide a fluid restricting or sealing connection with a female enteral feeding, of the type more fully described herein. However, it is emphasized that the plurality of embodiments of the closure assembly 10 as represented herein can, with little or no structural modifications, be used to establish a fluid restricting connection with a variety of different fixtures, connectors, etc. which are commonly used in the medical profession.

Figure 3:
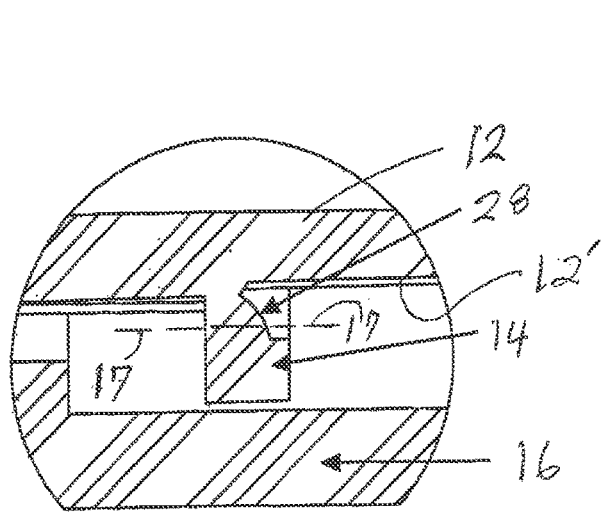
FIG. 3 is a transverse sectional view of a structural feature of one or more preferred embodiments of the closure assembly of the present invention.

In more specific terms, one or more preferred embodiments of the closure assembly 10 includes an end cap 12 having an initially attached indicator member 14, which may be in the form of an indicator ring or similar annular or curvilinear structure. The indicator member 14 is removably connected to an exterior surface 12' of the cap 12, as shown in FIGS. 3 and 3A, but may be movable with the cap 12 within the hollow interior 18 of the housing 16, while it is still attached thereto. In addition, the closure assembly 10 includes an exterior housing or sleeve 16 having a substantially hollow interior 18 which is dimensioned and configured to receive the cap 12, with the indicator member 14 connected thereto. Still referring to FIG. 1, the housing 16 includes an access opening 20 which is dimensioned and configured to facilitate passage of the cap 12 there-through. Therefore, the cap 12 can be removed from the interior of the housing 16, such as when connected to a corresponding fitting 100. As represented, the fitting 100 is structured in the form of a female fitting having exterior thread segments 102. Accordingly, attachment of the closure assembly 10 and more specifically the cap 12 is preferably, but not necessarily, accomplished by a threaded connection with the internal threads 103 formed on the interior portions of the cap 12, as clearly represented in FIGS. 6A-6D. As such, relative rotation between the fitting 100 and the cap 12 will facilitate a threaded connection of the thread segments 102 and the interior threads 103. With further reference to FIGS. 6A-6D, the flow sealing or flow restricting relation between the cap 12 and the female fixture 100 is accomplished by the insertion of a plug or like sealing member 105 into the fluid flow path 106 of the fixture 100.

Additional structural features of the housing 16 include a closed end 22 which may be in the form of a bottom end portion. The closed end or bottom end portion 22 may be connected by sealing to the remainder of the body 16 such as by heat seal, sonic welding, etc. In the alternative, the closed end portion 22 may be integrally formed with a remainder of the housing 16. As also represented, the closed end portion 22 is oppositely disposed to the aforementioned access opening 20.

Therefore, upon initial use the cap 12, with the indicator member 14 connected to an exterior surface 12' thereof, is disposed within the interior 18 of the housing 16. It is also of note that the access opening 20 is large enough to allow the cap 12 to pass there-through, such as when attached to the fixture 100. However, upon removal of the cap 12, the indicator member 14 will engage or abut against interior portions of the housing 16, causing its detachment from the exterior surface 12' of the cap 12, as represented in FIG. 2C.

Accordingly, one operative feature of the various preferred embodiments of the closure assembly 10 includes an effective indication that the cap 12 has been removed from the interior 18 of the housing 16 for use, such as when attached to a corresponding fixture 100. Further, any attempt to hide the fact that the cap 12 has been removed from the housing 16 will be evident by the inability to reattach the indicator member 14 to the exterior 12' of the cap 12, as explained hereinafter.

With reference to FIGS. 2B-2D, the closure assembly 10 is represented in various stages of use. More specifically, the fixture 100 is illustrated in an uninstalled state in FIG. 2A; but as shown in FIG. 2B, it is illustrated in an installed state, i.e., in a connected and ready to use or in use state; FIG. 2C illustrates the cap of the closure assembly as connected to a fixture and removed from the housing in a used state; FIG. 2D shows the cap and attached fixture is used and reinserted in the housing. Moreover, once the fixture 100 is connected to the cap 12 as intended and as represented in FIG. 2B, the cap 12 can be removed from the housing 16 through the access opening 20. Concurrently, the indicator member 14 will be detached from the cap 12 due to interfering engagement of the cap 12 with the interior portions of the housing 16, as represented in FIG. 2C. Once detached, the indicator member 14 will fall to the bottom of the housing 16, as in FIG. 2C, such as by gravity or otherwise be displaced into the represented detached orientation.

Therefore, FIGS. 2A-2D represent the indicator member 14 being first disposed in an attached orientation (FIGS. 2A-2B) and subsequently disposed in a detached orientation (FIGS. 2C-2D). Further, in at least the embodiment of FIGS. 1 and 2A-2D an effective and reliable indication that the indicator member 14 is detached from the cap 12 and loosely movable within the hollow interior 18 of the housing 16, is its ability to generate an audible sound. More specifically a manual manipulation or "shaking" of the housing 16 once the cap 12 has been removed from the interior 18, will result in a "rattling" type sound. This provides an effective indication that the cap 12 is in the detached orientation and that use or removal of the cap 12 and attached to fixture 100 has occurred.

Moreover, an attempted reinsertion of the cap 12 and connected fitting 100 into the interior 18 (FIG. 2D), will fail to establish a reconnection between the indicator member 14 and the cap 12. Accordingly, manipulation or shaking of the housing 16 will still generate an audible sound clearly indicating that the indicator member 14 is in its detached orientation.

As generally described, one structural and operative feature of the closure assembly 10, in one or more preferred embodiments, includes the indicator member 14 being detachable from the exterior surface 12' of the cap 12. As also indicated, this detachment of the indicator member 14 will occur substantially concurrent to the removal of the cap 12 from the interior 18 of the housing 16, such as through the access opening 20. Therefore, the removable connection of the indicator member 14 to the exterior of the cap 12 can be accomplished by at least one frangible tab 28. In certain practical applications, it may be preferred to include a plurality of frangible tabs 28 disposed in spaced relation to one another about the outer surface 12' of the cap 12. More specific structural details of each of the one or more frangible tabs 28 is represented in detail in FIGS. 3-3A. As disclosed, each of the one or more frangible tabs 28 is disposed in interconnecting relation between the interior surface 14' of the indicator ring or indicator member 14 and the exterior surface 12' of the cap 12.

Further, each of the one or more tabs 28 is structured to accomplish a predetermined, substantially precise "breakage" along the length thereof. The predetermined breakage is schematically indicated as 17 in FIG. 3 and is located in spaced relation to both the inner surface 14' of the indicator member 14 and the outer surface 12' of the cap 12, as shown in FIG. 3A. Therefore, the predetermined breakage 17 will occur at some point along the length of the one or more tabs 28 close to, but spaced from, the outer surface 12' of the cap 12. As a result, and as clearly represented in FIGS. 2C and 2D, and in detail in FIGS. 3-3A, tab segments 30 and 32 will be formed on the exterior surface 12' of the cap 12 and on the interior surface 14' of the indicator member or ring 14, respectively. In addition, at least one but preferably, each of the outer faces 30' and 32' of the tab segments 30 and 32 will have a substantially curvilinear configuration or other appropriate shape. As such, the outer faces 30' and 32' are shaped to substantially eliminate or significantly reduce the possibility of reconnection between the tab segments 30, 32 in the event the cap 12 is reinserted within the interior 18 (FIG. 2-D) in an effort to hide tampering or prior use. As a result, upon detachment of the indicator member 14 from the exterior surface 12' of the cap 12, the presence of the tab segments 30 and 32 on the respective outer faces 30' and 32' will assure that the indicator member 14 will not be "hung-up" or even temporarily reconnected, if there is an attempted reinsertion of the cap 12 into the housing 16, once the indicator member 14 has been detached.

Another preferred embodiment of the closure assembly 10 is represented in FIG. 4, FIGS. 5A-5D and FIGS. 6A-6D. With initial reference to FIGS. 5A-5D, the operative features thereof are the same as described with FIGS. 2A-2D. As such, the fixture 100 is disposed in an uninstalled state in FIGS. 2A and 5A; in and installed state in FIGS. 2B and 5B; in a connected and used state in FIGS. 2C and 5C and in a used and reinserted state in FIGS. 2D and 5D. The closure assembly 10 of FIG. 4 includes a housing or sleeve 116 having a hollow interior 18 and an upper section 117. In addition, the closure assembly 10 in this preferred embodiment, as well as one or more of the additional preferred embodiments includes a drive assembly 40. It is of note that the preferred embodiments of FIGS. 1 and 4, include the drive assembly 40 being substantially "centrally located" inwardly of corresponding sidewalls of the housing 116 and cap 12. Also, the drive assembly 40 includes two drive segments each connected to a different one of the interior surface of the bottom member 22 as well as to a corresponding interior, central portion of the cap 12 (not shown), to be described in greater detail hereinafter.

Figure 1:
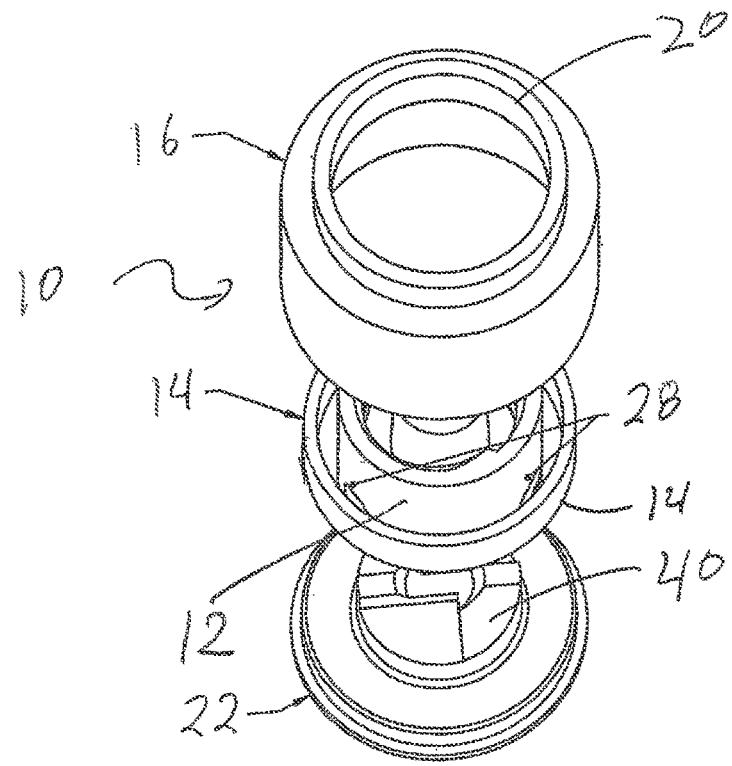
FIG. 1 is a perspective view in exploded form of one preferred embodiment of the closure assembly of the present invention.

Distinguishing structural features between the closure assemblies 10 of the embodiment of FIG. 1 and FIG. 4 include the presence of a viewing structure 42 formed in or integrated with the housing 116, such as in the sidewall thereof as represented in FIG. 4. The viewing structure 42 may be in the form of a viewing port or window 44. In the alternative, or in combination with the viewing port 44, a portion and or substantially the entirety of the housing 116, such as a sidewall portion 44', may be formed from a substantially transparent material. As used herein the term "substantially transparent" is meant to include a transparent and/or translucent material or any other material which allows sufficient light passage or clarity to facilitate viewing into the interior 18 of the housing 116. Such interior viewing will allow an observer to obtain a visual observance of one or more components disposed therein, as will also be explained hereinafter. For purposes of visually distinguishing the various components of the closure assembly 10 from one another, one or more of the interior components specifically including, but not limited to, the indicator member 14 are structured to include an "identifier". Such identifier may be in the form of a color coding, indicia, distinguishing markings, surface texture, or other visually distinguishing structures.

By way of example, the selected identifier may be in the form of "color coding", wherein one or more distinguishing colors are incorporated in the various components of the closure assembly 10. More specifically, the identifier may be incorporated in the indicator member or ring 14 and include a bright or vibrant distinguishing color. In turn, other interior components or portions of the housing 116, such as a shield 48 (FIGS. 6A-6D and FIGS. 7-7A) and/or the exterior surface 12' of the cap 12 may each be structured to include a distinguishing color which differ from one another. By virtue of such color coding, an observer can clearly determine whether the indicator member 14 is in the attached orientation, as represented in FIGS. 5A-5B and FIGS. 6A-6B or in a detached orientation as represented in FIGS. 5C-5D and FIGS. 6C-6D. More specifically, an observer will be able to determine whether the indicator member 14 is in the attached orientation or the detached orientation by the color appearing in the viewing port 44 or the color being observed through the transparent portion 44', as represented in FIGS. 5C-5D. Similarly, if the color being visually observed in the viewing port 44 and/or transparent portion 44' is not the assigned color of the indicator member, the observer will realize at the indicator member is in the attached orientation as represented in FIGS. 5A-5B and FIGS. 6A-6B. Such visual observance of the indicator member 14 or other components within the interior 18 of the housing 116 is a result of the indicator member 14 not being aligned with the window 44 and/or the transparent section 44' when in the attached orientation as clearly represented in FIG. 6A-6B. Instead, the viewing port 44 and/or transparent portion 44' may be aligned for visual observance of a shield 48 or like structure (FIGS. 6A-6B).

Therefore, the presence of an identifier such as in the form of "color coding" will enhance an observer's visual observation due to the fact that the shield 48 will be one distinguishing color and the indicator member 14 will be a different distinguishing color. As such, viewing of the interior 18 of the housing 116, when indicator member is in the detached orientation, as represented in FIGS. 5C-5D, occurs when the indicator member 14 is detached from the exterior 12' of the cap 12 and drops or falls down into the space generally indicated as 49, (see FIG. 7A) in front of the shield 48. Any attempt to reinsert the cap 12 into the interior of the housing 116, for purposes of hiding any attempted tampering will still allow an observer to have a visual observance of the indicator member 14 in front of the shield 48, within space 49 and in alignment with the viewing port 44 and or transparent portion 44'.

Figure 12A:
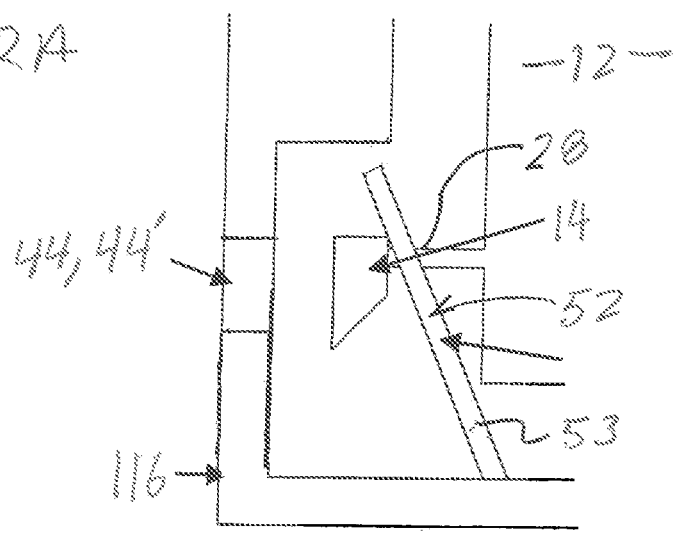
FIG. 12A is a schematic representation of one structural feature of a retaining assembly which may be associated with one or more preferred embodiments of the closure assembly of the present invention.
Figure 12B:
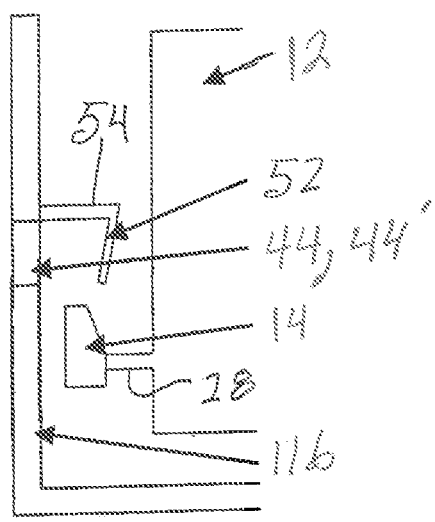
FIG. 12B is a schematic representation of yet another structural feature of the retaining assembly, differing from the structure of FIG. 12A, which may be associated with one or more preferred embodiments of the closure assembly of the present invention.

FIGS. 12A-12B disclose a structural and operative modification of the embodiment of FIG. 4 which includes a retaining structure, or assembly generally indicated as 52. The retaining assembly 52 may be used to engage and maintain the indicator member 14 in alignment with the window 44 and/or transparent portion 44'. Therefore, upon removal of the cap 12 and detachment of the indicator member 14 there from, a preloaded or inherently biased segment 53 may engage the indicator member 14. Such engagement will force or maintain the indicator member 14 in aligned relation with the viewing port 44 and/or transparent portion 44'. Somewhat similarly, in the embodiment of FIG. 12B, the retaining member 54 is disposed and structured to receive and retain the indicator member 14, upon it being detached from the cap 12. More precisely, as the cap 12 is raised through the access opening 20 of the housing 116, the indicator member 14 will move with the cap 12 into engagement with the retaining member 54. Upon a completed detachment of the indicator member 14 from the exterior surface 12', the indicator member 14 will be forced into engagement with the retaining member 54 in its detached orientation. When so disposed, the indicator member 14 will be in alignment with the viewing port 44 and/or transparent portion 44'. An observer will thereby be provided a clear visual observance of the retained indicator member 14. It is again emphasized that in the embodiment of FIGS. 12A-12B, the identifier, such as but not limited to a color coding, may be associated with the indicator member 14 and/or the remaining components within the interior 18 of the housing 116.

As noted above, the viewing structure 42 being in the form of the viewing port or window 44 can be used in combination with or separately from the transparent portion 44' of the sidewall of the housing 116. At least one additional option would be the ability to observe "extended color indication", through a transparent portion 44' of the housing 116. As such, the closed end 22 of the cap 12 could include a distinguishing color. The indicator member or ring 14 could be the same or other, possibly complementary, distinguishing color. However, in this additional option, before the indicator member is detached from the cap 12 it will be in the attached orientation. The attached orientation of the indicator member 14 will not be initially viewable through the transparent portion 44'. Such non-observance could be the result of the indicator member 14 being positioned behind the shield like structure 48, such as in a space 49', rather than being in the space 49 in front thereof, as represented in FIG. 7A. However, when the indicator member 14 is in a detached orientation, because of a removal of the cap 12 and fixture 100 from the housing 116, it would be lifted out of the space 49' and disposed in visual observance through the substantially transparent portion 44'. Due to the fact that the indicator member 14 and the lower end portion 22 of the housing 116 would then be concurrently viewable through the transparent portion 44', both the color of the indicator member 14 and the lower end portion 22 would be exposed. This would result in a concurrent visual observance of the colors of the bottom and portion 22 and indicator member 14 or an "extended color indication". This, in turn, would be indicative that the cap 12 and fixator 100 had been removed and possibly used.

Accordingly, the use of an appropriate and visually distinguishable "identifier" being incorporated in the structure of the indicator member 14 and other components of the closure assembly 10 provide a reliable indication of prior use and possible tampering. It is further emphasized that the indicator member 14 may be indicative of prior use and/or tampering when it is disposed in either the attached orientation or the detached orientation. It is further emphasized that the structural and operative features of at least the embodiment of FIGS. 4 and 8 may be structurally arranged or modified such that the indicator member 14 may provide a visual indication of the indicator member 14 being in an attached orientation or the detached orientation by it being visible or not being visible, through the viewing structure 42.

Figure 8A:
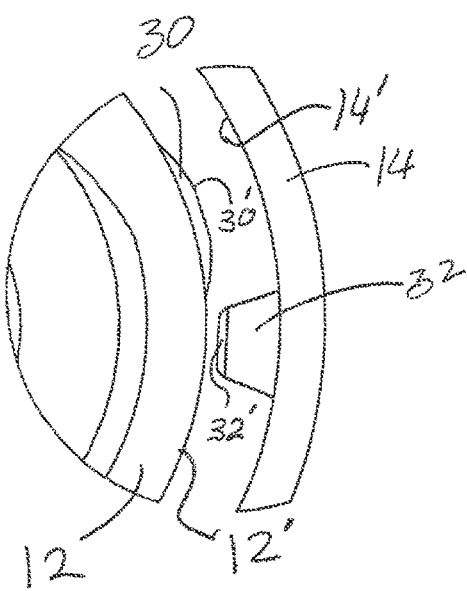
FIG. 8 is a perspective view in exploded form of yet another preferred embodiment of the closure assembly of the present invention.
Figure 8:
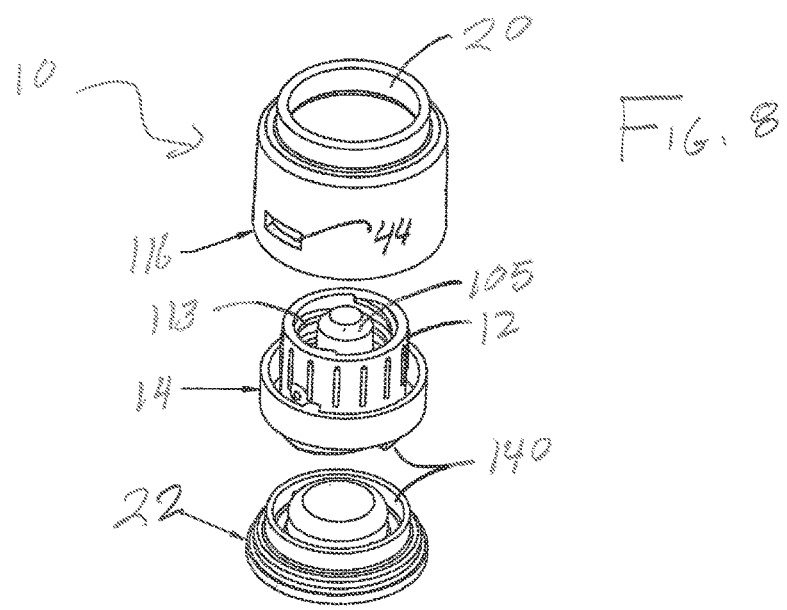
Figure 9A:
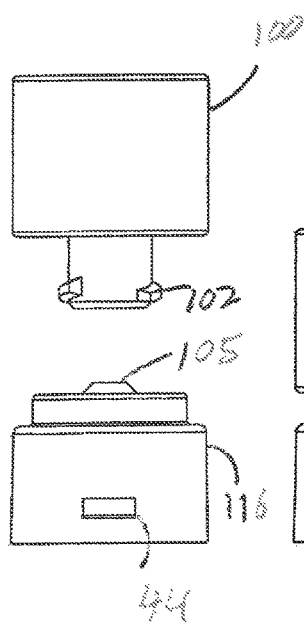
FIG. 9A is a front view of the embodiment of FIG. 8 in an uninstalled state.
Figure 9B:
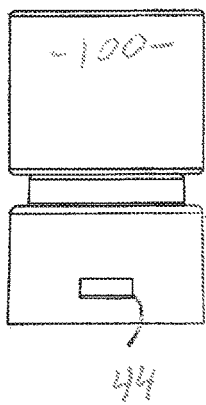
FIG. 9B is a front, partial interior view of the embodiment of FIG. 8 in an installed state.
Figure 9C:
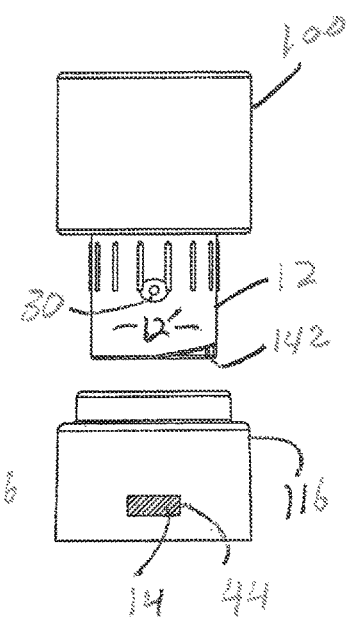
FIG. 9C is a front partial interior view of the embodiment of FIG. 8 wherein a cap of the closure assembly is connected to a fixture and removed from the housing in a used state.
Figure 9D:
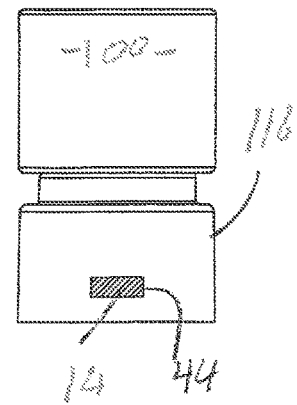
FIG. 9D is a front partial interior view of the embodiment of FIG. 8 wherein the cap and attached fixture is used and reinserted in the housing.

Yet another preferred embodiment of the closure assembly 10 is represented in an unassembled state in FIG. 8.

Structural and operative details of the closure assembly 10 of FIG. 8 are further represented in FIGS. 9A-9D; FIGS. 10A-10B and FIGS. 11A-11B. It is to be noted that the FIGS. 9A-9D are operatively similar to what is illustrated in FIGS. 2A-2D and FIGS. 5A-5D, at least in terms of being in an uninstalled state in FIG. 9A; and in an installed state as in FIG. 9B; in a used state as in FIG. 9C and in a used and reinserted state, as in FIG. 9D. Therefore, the closure assembly 10 of FIG. 8 includes a housing 18 having a closed bottom or end portion 22 defining a hollow interior 18 with an access opening 20. Further, a cap 12 structured to be connected in flow restricting relation to a fitting 100 includes an indicator member or ring 14 removably connected to the exterior thereof by one or more frangible tabs 32 as described in detail above. In addition, the housing 116 may also include a viewing structure 42 in the form of a viewing port or window 44 and/or a transparent portion 44' as also described above.

Distinguishing features of the preferred embodiment of the closure assembly 10 of FIG. 8 are represented in detail in FIGS. 10A-10B and FIGS. 11A-11B. More specifically, the closure assembly 10 of FIG. 8 includes a drive assembly 140 which is structured to define a concurrent single direction, driven rotation of the cap 12 and a housing 116. Therefore, attempted rotation of the housing 116 in a predetermined first direction, such as a clockwise direction, which may establish a threaded connection with the fixture 100, will result in the concurrent rotation of the housing and the cap 12 with one another. However, rotation in a second or opposite direction to the aforementioned first direction will result in a "slippage" and/or relative movement between the housing 116 and cap 12. Such an opposite, possibly counterclockwise rotation, may be attempted when one tries to remove the cap 12 from the fixture 100 by unscrewing the cap 12.

Therefore, the drive assembly 140 comprises and may be accurately described as an exteriorly located "ramp and cliff" drive structure. As should be apparent, the exterior location of the drive assembly 140 is distinguishable from the central location of the "ramp and cliff" drive assembly 40 of the embodiments of FIGS. 1 and 4. With primary reference to FIGS. 10A-10B and FIGS. 11A-11B, the exterior ramp and cliff drive structure 140 comprises a first drive component 142, mounted on an open ended side wall or skirt 119, preferably at a lower end of the sidewall of the cap 12. Even more specifically, the first drive component comprises a series of "ramps" 142' and one or more "cliffs" 142" collectively extending about a circumferential edge or peripheral perimeter of a lower end or other appropriate portion of the skirt or sidewall 119 of the cap 12. In cooperation therewith, the exterior ramp and cliff drive assembly 140 also includes a second drive component 144 formed on an inner surface of the housing 116 and preferably on an inner, end surface of the bottom end member 22. The second drive component 144 also includes a plurality of "ramps" 144' and a plurality of "cliffs" 144" collectively disposed in a circular, curvilinear or other continuous configuration corresponding to the circumferential edge or periphery of the skirt or sidewall 119 of the cap 12 on which the first drive segment 142 is formed. In addition, the second drive segment 144 may be disposed in a recessed location within a channel 146 defined by a circular or curvilinear ledge or like structure 148.

Figures 10A, 10B:
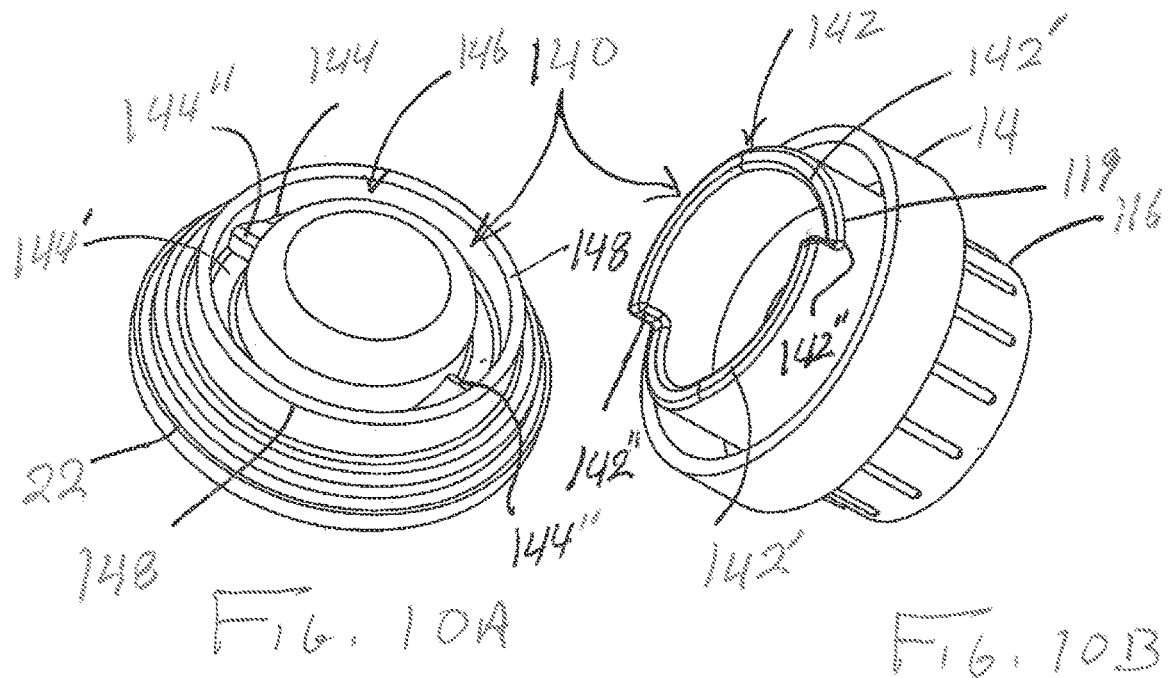
FIGS. 10A and 10B are perspective detail views of drive segments of a common drive assembly associated with one or more preferred embodiments of the closure assembly of the present invention, including the embodiment of FIG. 8.
Figures 11A, 11B:
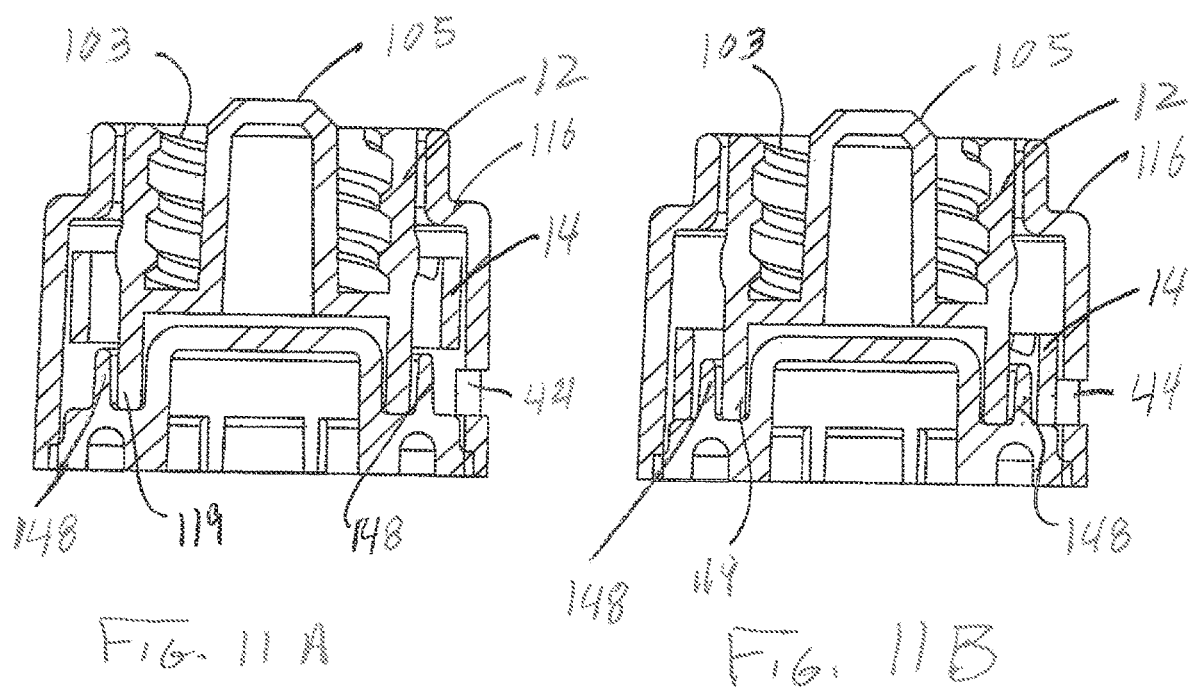
FIG. 11A is a sectional view of one or more preferred embodiments of the drive assembly as represented in the embodiments of FIG. 8 and FIGS. 10A-10B.
FIG. 11B is a sectional view of one or more preferred embodiments of the drive assembly as represented in the embodiments of FIG. 8 and FIGS. 10A-10B.

As set forth above with regard to FIGS. 10A-10B, disposition of the cap 12 within the interior 18 of the housing 116, prior to connection with the fitting 100, will result in a movable, sliding, mating engagement between the first and second drive segments 142 and 144, when the housing is rotated in a predetermined second direction. Due to the operative nature of the ramp and cliff structure of each of the drive segments 142 and 144, rotation of the housing 116 in a predetermined first direction, such as a clockwise direction, will result in a concurrent rotation of the cap 12. Such concurrent rotation in the first predetermined or clockwise direction will be due to an abutting engagement with corresponding cliff segments 142" and 144". However, rotation of the housing in an opposite or counterclockwise direction will result in a relative movement or slippage between the housing 116 and the cap 12, as set forth above, due to a non-abutting confrontation between the cliff segments 142" and 144" and a sliding engagement between the ramps segments 142' and 144'.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A tamper evident closure assembly for a medical fitting, said closure assembly comprising:
 a cap connectable in flow restricting relation to the medical fitting,
 an indicator member removably connected to an exterior of said cap,
 a housing including an at least partially hollow interior and an access opening,
 said cap movably and removably disposed within said hollow interior concurrent to connection to the medical fitting,
 said indicator member movable with said cap when connected thereto and movably disposed in a detached relation from said cap in a captured, detached orientation within said housing, upon removal of said cap from said housing, and
 a viewing structure formed in a sidewall of said housing and disposed and structured to define a visual observation of components within said housing.

2. The closure assembly as recited in claim 1 wherein said viewing structure comprises said sidewall of said housing being at least partially formed from a substantially transparent material.

3. The closure assembly as recited in claim 1 wherein said viewing structure comprises a viewing port integrally formed in said sidewall.

4. The closure assembly as recited in claim 3 wherein said viewing structure is disposed to establish said visual observation of said indicator member when in said captured, detached orientation within said housing.

5. The closure assembly as recited in claim 4 further comprising at least one retaining member disposed and structured to retain said indicator member in said visual observation when in said captured, detached orientation.

6. The closure assembly as recited in claim 3 wherein said viewing port is disposed to establish said visual observation with said indicator member when in said captured, detached orientation within said housing; said visual observation being indicative of removal of said cap from said housing.

7. The closure assembly as recited in claim 6 wherein a non-visual observation of said indicator member through said viewing port is indicative of non-removal of said cap from said housing.

8. The closure assembly as recited in claim 3 wherein said indicator member comprises an identifier disposed thereon and structured to visually distinguish said indicator from at least one of said components within said housing.

9. The closure assembly as recited in claim 8 wherein said identifier comprises a color coding.

\* \* \* \* \*